United States Patent [19]

Falholt

[11] Patent Number: 4,973,417

[45] Date of Patent: Nov. 27, 1990

[54] ENTERIC COATED DETERGENT ENZYMES

[75] Inventor: Per Falholt, Gentofte, Denmark

[73] Assignee: Novo Industri A/S, Bagsvaerd, Denmark

[21] Appl. No.: 144,175

[22] Filed: Jan. 15, 1988

Related U.S. Application Data

[63] Continuation-in-part of Ser. No. 000,057, May 19, 1987.

[30] Foreign Application Priority Data

May 21, 1986 [DK] Denmark ............................ 2355/86
Dec. 3, 1986 [DK] Denmark ............................ 5805/86

[51] Int. Cl.[5] ....................... C11D 3/386; C11D 3/39; C11D 17/08; C12N 9/96

[52] U.S. Cl. ....................................... 252/95; 252/100; 252/174.12; 252/174.13; 252/174.17; 252/174.24; 427/213; 435/187; 435/188

[58] Field of Search ................ 252/91, 174.12, 174.13, 252/DIG. 12, 95, 100, 174.24; 427/213; 435/187, 188

[56] References Cited

U.S. PATENT DOCUMENTS

| | | | |
|---|---|---|---|
| 3,723,327 | 3/1973 | Van Kampen | 252/110 |
| 3,975,280 | 8/1976 | Hachmann | 252/102 |
| 3,997,459 | 12/1976 | Bogie | 252/99 |
| 4,011,169 | 3/1977 | Diehl | 252/95 |
| 4,090,973 | 5/1978 | Maguire | 252/174.13 |
| 4,106,991 | 8/1978 | Markussen | 435/187 |
| 4,303,542 | 12/1981 | Heinlein | 252/91 |
| 4,707,287 | 11/1987 | Herdeman | 252/91 |
| 4,790,881 | 12/1988 | Wittwer | 106/189 |

FOREIGN PATENT DOCUMENTS

| | | | |
|---|---|---|---|
| 763681 | 9/1971 | Belgium | 252/174.12 |
| 888632 | 10/1981 | Belgium . | |
| 1000628 | 11/1976 | Canada | 252/DIG. 12 |
| 2058421 | 5/1971 | France . | |
| 1294557 | 11/1972 | United Kingdom . | |
| 1362365 | 8/1974 | United Kingdom . | |
| 1554482 | 10/1979 | United Kingdom . | |
| 2135347A | 8/1984 | United Kingdom . | |

*Primary Examiner*—Dennis Albrecht
*Attorney, Agent, or Firm*—Morris Fidelman; Franklin D. Wolffe

[57] ABSTRACT

The granulate detergent enzyme product comprises a core of a microbial enzyme containing material with an enteric coating. Due to the coating the enzymatic stability is enhanced, in the presence of other detergent components, espacially strong bleaching agents. The coating is usually carried out in a fluid bed. Also coatings with antioxidants and acid coatings enhance the enzymatic stability.

11 Claims, No Drawings

ENTERIC COATED DETERGENT ENZYMES

This application is a continuation-in-part under 35 USC 120 and 35 USC 365(c) of United States International application PCT DK 87/00057, filed May, 19, 1987.

TECHNICAL FIELD

The technical field to which this invention pertains comprises a granulate detergent enzyme product comprising a core of a microbial enzyme containing material and a coating, a method for production of such product, a use of such product, and a detergent or a detergent component containing such product.

BACKGROUND ART

The field of enzymatic detergent additives has been rapidly growing during the last decades. Reference is made to the article "How Enzymes Got into Detergents", vol. 12, Developments in Industrial Microbiology, a publication of the Society for Industrial Microbiology, American Institute of Biological Sciences, Washington, D.C. 1971, by Claus Dambmann, Poul Holm, Villy Jensen and Mogens Hilmer Nielsen, to the article "production of Microbial Enzymes", Microbial Technology, Sec. ed., Vol. I, Academic Press, 1979, pages 281-311, by Knud Aunstrup, Otto Andersen, Edvard A. Falch and Tage Kjaer Nielsen, and to Pl.N. Christensen, K. Thomsen and S. Branner: "Development of Detergent Enzymes", a paper presented on Oct. 9, 1986, at the 2nd World Conference on Detergents held in Montreux, Switzerland.

The most common enzymatic detergent additive is a proteolytic additive, but also amylolytic, cellulolytic, and lipolytic detergent additives are suggested, e.g., in GB patent No. 1 554 482, BE patent No. 888 632, and U.S. Pat. No. 4,011,169, column 4, line 65 to column 5, line 68. The above list of enzymes is not exhaustive, but represents the most common enzymatic detergent additives.

Enzymatic detergent additives for use in powder detergents are usually prepared in the form of dust-free granulates. These granulates can be produced in several different ways. Reference can be made to GB patent No. 1 362 365 which describes the production of enzyme containing granulates used as detergent additives by means of an apparatus comprising an extruder and a spheronizer (sold as MARUMERIZERR), and to U.S. Pat. No. 4 106 991, which describes the production of enzyme containing granulates used as detergent additives by means of a drum granulator. Reference is also made to European patent publication EP-A No. 0170360 which describes enzyme granulates containing certain salts to improve the storage stability.

Whereas enzyme granulates prepared according to known methods are entirely satisfactory for use in many commercial powder detergents, enzyme stability of these granulates is reduced in certain detergent formulations and at certain storage conditions. These include particularly detergents with high water content and/or high pH and/or high content of bleaching agents and particularly by storage at high humidity and temperature.

In FR patent No. 2.058.421 a method for production of detergent or bleaching agents containing enzymes protected with a coating of an enteric coating agent is described. However, the inventor hereof has shown that the protective effect, i.e., the improvement of enzymatic stability, is variously absent, very small or even negative, probably due to the fact that the particle size of the powder is too small in comparison to the (small) amount of coating agent used, and the coating agent is not coated on the powder in an optimal manner. Also, the method involves the use of a solution of the coating agent in an organic solvent.

Thus, a need exists for an easier and more efficient method for production of a particulate detergent enzyme product which is modified in such manner that the enzymatic stability is improved considerably in adverse detergent formulations and/or at adverse storage conditions, whereby this modification in no regard should impair any process or material related to the continued storage and later use of the product.

DISCLOSURE OF THE INVENTION

After considerable research, on new additives and/or coatings, and application techniques for such coatings it has been discovered that a coating of the particulate detergent enzyme with one specified category of coating agents, (out of the many possibilities known in the art), combined with a specific coating technique will modify the particulate detergent enzyme in the wanted manner, i.e. this coating will improve the enzymatic stability at adverse conditions, without any accompanying unwanted side effects.

Thus, the granulate detergent enzyme product according to the invention comprises a core of a microbial enzyme-containing material and a coating thereon, wherein the coating comprises an enteric coating agent, and wherein more than 90% of the granulate cores exhibit particle sizes between 2 and 2000 μm, preferably between 250 and 2000 μm, more preferably between 250 and 1000 μm; wherein the weight of the coating agent applied to the granulate cores is between 5 and 30% of the weight of the coated product, preferably between 5 and 20% of the weight of the product.

The method according to the invention for production of a granulate detergent enzyme product comprising a core of a microbial enzyme containing material and a coating of an enteric coating agent thereon, whereby the weight of the enteric coating agent of between 1 and 40% of the weight of the product may be applied including between 1 and 5% of the weight of the product which sometimes is advantageous. The method is characterized by the fact that the cores of the microbial enzyme containing material and an aqueous dispersion of the coating agent are introduced into a fluid bed drying apparatus, whereafter the material leaving the apparatus is collected as the product.

It is an important advantage that it is unnecessary to use any organic solvents during the production. If, however, the use of organic solvents for some reason should be desired, organic solvents can be used as well. The fluid bed method can be carried out batchwise or continuously.

Any fluid bed method can be used in the method according to the invention, e.g., a usual fluid bed process, a Wurster bed process or a rotor bed (Glatt) process (vide e.g., David M. Jones, "Factors to consider in fluid-bed processing", Pharmaceutical Technology, April 1985).

However, any other process than a fluid bed process by means of which a satisfactory coating can be applied on a particulate material without unwanted agglomeration due to adhesion between particles, is considered a technical equivalent insofar as concerns the granulate detergent enzyme product and can be used, e.g., a coating pan process or a coating process or a coating process in a mixer (e.g., a Lodige mixer) can be used for manufacture of the product according to the invention. If more than one coating is to be applied to the particulate material, each individual coating can be applied by any usable coating method.

In this specification the detergent concept is to be understood in a broad sense. Thus, the term granulate detergent enzyme product is intended to include any granulate enzyme product intended for detergency usage and which is a part of or is intended to become a part of any cleaning or cleansing composition, e.g., a bleaching agent, a softener, a color clarification agent or a pure surfactant. Further, the detergent according to the invention comprises any cleaning or cleansing composition containing the product according to the invention, and the detergent component according to the invention comprises for instance a bleaching agent, a softener, a color clarification agent or a pure surfactant. Further, the detergent according to the invention comprises any cleaning or cleansing composition containing the product according to the invention, and the detergent component according to the invention comprises for instance a bleaching agent, a softener, a color clarification agent or a pure surfactant containing the product according to the invention.

The invention is only concerned with microbially produced enzymes, as other enzymes are not believed to be suited as enzymatic detergent additives, mainly due to cost and stability considerations.

In the pharmaceutical art an enteric coating is a well defined material, i.e., a special coating applied to tablets or capsules which prevents release and absorption of their contents until they reach the intestines. For a description of a typical enteric coating agent reference can be made to e.g., Manufacturing Chemist, August 1986, p. 35–37. It is to be understood that most, maybe all enteric coating agents which can be used in the pharmaceutical field, can be used in the invention as well. Typical examples of enteric coating agent are: cellulose acetate phthalate (Cellacephate®, CAP), vinyl acetate crotonic acid copolymer (Luviset®), methacrylic acid, (meth)acrylic acid ester copolymer (Eudragit®), hydroxypropyl methylcellulose phthalate.

Due to the nature of an enteric coating the particulate detergent enzyme product according to the invention exhibits most favorable stability in the presence of powerful acid bleaching agent. Such powerful acid bleaching agents are described e.g., in Fette Seifen Anstrichmittel 88' Jahrgang, Nr. 5, 1986, 159-165, and GB patent No. 2,135,347 A. According to U.S. home laundering practice powerful acid bleaching agents are added separately from the detergent to the washing machine, i.e. are not previously mixed with the other alkaline detergent components. Thus, the particulate detergent enzyme produced according to the invention may be mixed with such acid bleaching agent.

If the particulate detergent enzyme product is added to other detergent components of an alkaline nature, the stability enhancing effect may be lowered, due to the solubility of the enteric coating at high pH-values. However, in such instances special precautions for keeping stability at a high level may be taken, as is explained later in more detail.

The enteric coating agent does not generate any disturbing influence during the washing process, as it will dissolve in the washing liquid (which typically are of a pH value at which the enteric coating agent is easily soluble) whereafter the enzyme can exert its wanted activity on the laundry. Also, especially in a damp atmosphere and at relatively high temperatures it has been found that the enzymatic stability is satisfactory during storage of the product according to the invention in the presence of powerful bleaching agents.

In Acta Pharmaceutical Technologica 31 (1) 1985, p. 38–41 non-enteric and enteric film coating of commercial pancreatin tablets is described. From FIG. 2(B) of this paper it appears that the enzyme stability of the non-coated tablets and the tablets coated with Eudragit® L is not an advantageous coating agent for pancreatin tablets in the pharmaceutical field.

GB patent No. 1 294 557 discloses a method for production of micro capsules containing a detergent enzyme during which a binder, which can be a copolymer of acrylic acid, is used. However, in the known process micro capsules comprising a homogeneous mixture of soluble, inorganic salt, binder and enzyme, are produced, rather than the enzyme containing particles coated with a coating which is specified both in regard to composition and permeability according to the invention. Also, the known micro capsules do not offer the technical advantage exhibited by the product according to the invention.

In Japanese patent publication No. JP-60-190-,497A a method for production of an enzymatic detergent composition is described during which a copolymer containing aliphatic unsaturated discarboxylic acid monomer in an aqueous medium is used. However, in contradistinction to the present invention no impermeable coating for protection of the detergent enzyme is suggested.

In FR patent No. 2.058.421 a method for production of detergent or bleaching agents containing enzymes protected with a coating of an enteric coating agent is described. However, the inventor hereof has shown that the coating effect, i.e., the improvement of enzymatic stability, is absent, very small or even negative, probably due to the fact that the particle size of the powder is too small in comparison to the small amount of coating agent used, and the coating agent is not coated on the powder in an optimal manner.

In a preferred embodiment of the method according to the invention more than 90% of the enzyme granulate cores exhibit particle sizes between 2 and 2000 μm. This particle size range is most useful for a granulate detergent enzyme product.

In a preferred embodiment of the method according to the invention more than 90% of the granulate cores exhibit particle sizes between 2 and 100 μm. This size range of granulate is specially suited as a constituent in a suspension containing this granulate and a strong acid bleaching agent.

In a preferred embodiment of the method according to the invention more than 90% of the granulate cores exhibit particle sizes between 250 and 1000 μm. This size range of granulate is specially well suited as a constituent in a granulate detergent formulation comprising a bleaching agent and alkaline detergent components.

In a preferred embodiment of the method according to the invention the weight of the coating agent applied to the granulation core is between 10 and 30% of the weight of the coated product. If the weight of coating agent is less than 10% the satisfactory stabilizing effect is not obtained, and with a weight of coating agent above 3% only a little improvement in stability is obtained.

In a preferred embodiment of the method according to the invention the weight of the coating agent is between 5 and 20% of the weight of the product. A product with this coating is especially well suited for relatively small particles or particles containing sensitive enzymes.

In a preferred embodiment of the method according to the invention the enteric coating agent is a copolymer of a (meth)acrylic acid or derivative thereof and another (meth)acrylic acid or derivative thereof. It goes without saying that only copolymers with film forming characteristics can be used, e.g., copolymers with a molecular weight above around 100,000 beyond which molecular weight most properties do not change with the exception of viscosity (in solution). Copolymers of this type is sold under the trade mark Eudragit® (Rohm Pharma, GmbH, Darmstadt, Postfach 4347, West Germany) and it has been found that the Eudragit® copolymer is able to form an impermeable enteric coating.

In a preferred embodiment of the method according to the invention the copolymer is a copolymer of methacrylic acid and an acrylic acid ester, preferably a methyl or ethyl ester. Such a product is commercially available under the trade mark Eudragit® L 30 D. This enteric coating agent can be applied as an aqueous emulsion in a fluid bed coating process, and thus the use of organic solvents can be avoided.

It appears from the brochure "Eudragit L und S", "Prospekt (Info L/S-1)", published by Rohm Pharma GmbH, D-6100 Darmstadt, Postfach 4347, West Germany that Eudragit L 30D has a solubility of zero at pH=6, whereas the solubility rises rapidly for pH values above 6.

In a preferred embodiment of the product according to the invention the copolymer is a copolymer of methacrylic acid and methacrylic acid methyl ester. Such a product is commercially available under the trade mark Eudragit® L/S. This enteric coating agent can be applied as an organic solution in a fluid bed process, and a coating with a high permeability is thereby obtained.

In a preferred embodiment of the method and product according to the invention the coating agent contains between 25 and 100% of the enteric coating agent (on a dry substance basis). If the coating agent contains less than 25% of the enteric coating agent, the impermeability of the coating is not satisfactory.

In a preferred embodiment of the method and product according to the invention the part of the coating agent which is not the enteric coating agent is a filler, preferably $CaCO_3$, talc and/or $TiO_2$, and/or a plasticizer, preferably PEG and/or PVP. The filler may be added for economic and/or cosmetic purposes, and the plasticizer can be added to improve the flexibility of the coating. However, the coating agent can consist of enteric coating agent entirely, and also, other additives than fillers and plasticizers may be present in the coating agent.

In a preferred embodiment of the method and product according to the invention the enzyme is one or more of a protease, an amylase, a lipase, a cellulase, and an oxidase. These are the most commonly used detergent enzymes. Practice of the invention applies to any detergent enzyme.

In a preferred embodiment of the method and product according to the invention the particles of enzyme containing material are commercially available granulates. Usually these granulates are already coated but their coating does not generate a satisfactory enzyme stability in the presence of powerful bleaching agents. Such particles are easily available and are well suited for the invention.

In a preferred embodiment of the method and product according to the invention the particles already possess or are given a coating containing or consisting of an antioxidant, preferably as an undercoat to the enteric coating. This embodiment is specially well suited in such cases in which the granulate detergent enzyme product is mixed with a powerful bleaching agent. In that case small amounts of humidity saturated with bleaching agent may diffuse into the enzyme granules, even through the enteric coating, and impair the stability of the enzyme. In this embodiment, however, the antioxidant in the undercoat reacts with the bleaching agent and thus improves the enzyme stability.

In a preferred embodiment of the method and product according to the invention the particles possess a coating containing or consisting of an acid material, preferably as an overcoat on the enteric coating. This embodiment is specially well suited, when it is intended to mix the product according to the invention with alkaline detergent components. In such instances the solubilizing capability of the alkaline detergent components on the enteric coating is inhibited, and thus, the stability of the product according to the invention will be enhanced.

In a preferred embodiment of the method and product according to the invention any two of the three coatings o all three coatings are united to one single, combined coating. This is an advantage from the production point of view.

The method described in the previously indicated FR patent No. 2.058.421 involves the use of a solution of the coating agent in an organic solvent. An organic solvent is unnecessary in order to perform the method according to the invention.

Also, the invention comprises a use of the granulate detergent enzyme product prepared according to the invention as a constituent of a detergent or of a detergent component.

In a preferred embodiment of the use according to the invention the product exhibits a particle size interval characterized by the fact that 90% of the granulate cores exhibit particle sizes between 2 and 100 μm, and the detergent or the detergent component appear as a slurry. In this manner a physically stable mixture can easily be obtained by addition of sedimentation inhibition agents.

In a preferred embodiment of the use according to the invention the product exhibits a particle size interval characterized by the fact that 90% of the granulate cores exhibit particle sizes between 250 and 1000 μm, and the detergent or the detergent component appear as a particulate material. In this matter it is possible to obtain a mixture, the homogeneity of which does not change with time.

In a preferred embodiment of the use according to the invention the product exhibits a particle size interval characterized by the fact that 90% of the granulate cores exhibit particle sizes between 250 and 1000 μm, the detergent component appear as a particulate material, and the detergent component is an acid bleaching agent. It has been found that the stability of the product is satisfactory even in the presence of powerful acid bleaching agents.

Finally, the invention comprises a detergent or a detergent component, containing as a constituent the product prepared according to the invention.

In a preferred embodiment of the detergent or detergent component according to the invention the product exhibits a particle size interval characterized by the fact that 90% of the granulate cores exhibit particle sizes between 2 and 100 μm, and the detergent or the detergent component appear as a slurry. In this manner a physically stable mixture can easily be obtained by addition of sedimentation inhibition agents.

In a preferred embodiment of the detergent or detergent component according to the invention the product exhibits a particle size interval characterized by the fact that 90% of the granulate cores exhibit particle sizes between 250 and 1000 μm, and the detergent or the detergent component appear as a non-dusting granulate. In this manner it is possible to obtain a mixture, the homogeneity of which does not change with time.

In a preferred embodiment of the detergent or detergent component according to the invention the product exhibits a particle size interval characterized by the fact that 90% of the granulate cores exhibit particle sizes between 250 and 1000 μm, the detergent component appear as a particulate material, and the detergent component is an acid bleaching agent. It has been found that the stability of the product is satisfactory even in the presence of powerful acid bleaching agents.

The invention will be illustrated by means of the following examples. Some of the examples form products outside the scope of the invention; the products of those examples are to be considered as comparison examples.

MODES FOR CARRYING OUT THE INVENTION, INCLUDING BEST MODE

EXAMPLE 1

The following enzyme containing products used as starting materials will appear in this example.

| Code | Short designation | Characterization |
|---|---|---|
| 1 | Alcalase protease, chloride based | The granulate is produced as in example IV in U.S. Pat. No. 4,106,991 and subsequently coated with a 20% w/w coating comprising $TiO_2$ and PEG. |
| 2 | Alcalase protease sulphate based | Produced as 1, but NaCl is substituted by the same amount of $Na_2SO_4$. |
| 3 | Termamyl amylase, chloride based | Produced as 1, but 7.5 kg of ALCALASE ® is substituted by 6.7 kg of TERMAMYL concentrate giving rise to an end product of 60 KNU/g (vide U.S. Pat. No. 4,106,991) |
| 4 | Termamyl amylase, sulphate based | Produced as 3, but NaCl is substituted by the same amount of $Na_2SO_4$. |

These four enzyme products are commercially available granulates; they were used as controls and as starting materials for production of the products prepared according to the invention. On the basis of the starting materials 2 and 4 products were produced according to the invention in the following manner 2 or 4 were introduced into a fluid bed drying apparatus with 15 kg/charge, and simultaneously a 30% aqueous dispersion of Eudragit ® L 30 D was introduced at a rate of 4.5 kg/hour together with inlet air of a temperature of 60° C. to yield a product consisting of the starting material coated with 9% Eudragit ® L 30 D. The corresponding two products according to the invention are designated 2i and 4i.

The six products 1,2, 3 and 4 (prior art products) and 2i and 4i (products prepared according to the invention) were mixed with a detergent containing around 4% of an acid bleaching agent in a proportion of 1% w/w. The mixtures are Storage stability tests on the six mixtures were carried out both in vessels with controlled humidity and in closed vessels (dry). The results are tabulated below.

TABLE 1

| | | Residual activity, % | | | | | | |
|---|---|---|---|---|---|---|---|---|
| | Time, | Mixture | | | | | | |
| | Weeks(s) | M1 | M2 | M2i | M2i | M3 | M4 | M4i |
| 30° C., humidity | 1 | 1 | 34 | 53 | 46 | 2 | 2 | 9 |
| cycle: | 2 | 1 | 18 | 27 | 26 | | | |
| 8 h 80% r.h. | 3 | 1 | 10 | 20 | 16 | | | |
| 16 h 60% r.h. | | | | | | | | |
| 37° C. | 2 | 55 | 52 | 46 | — | | | |
| closed | 4 | 38 | 33 | 35 | 40 | | | |
| vessels | 8 | 24 | 20 | 23 | 26 | | | |

The stability tests clearly show that the coating of the product prepared according to the invention exerts the stability improving effect only in the presence of humidity, when mixed with a powerful oxidizing agent. In a dry atmosphere the stability is satisfactory already in the absence of the coating on the product prepared according to the invention.

EXAMPLE 2

The formulation of the raw granulate, i.e. the totally unprotected granulate core, is as follows:

15% of fibrous cellulose
9% of carbohydrate binder
4% of $TiO_2$
ad 100% of $Na_2SO_4$/ALCALASE ® concentrate ALCALASE ® (Novo Industri A/S) is a Bacillus licheniformis proteinase.

This raw granulate is produced in such enzyme strength which after the coating will generate a final proteolytic activity of 2.0 Anson units/g. Except for differences in composition the production of the raw granulate is carried out as described in U.S. Pat. No. 4,106,991, example I.

The primary coating of the raw granulate is carried out as indicated in U.S. Pat. No. 4,106,991, example XXII and consists of 7% PEG 4000 and 9% $TiO_2$, the percentages being calculated in relation to the weight of the raw granulate. This product is designated ALCALASE ® T 2.0.

The process parameters in relation to the application of the three coatings indicated in the following (in relation to e.g. temperatures, spray pressure and spray rate) and of the coatings in the following examples were as indicated in the section "Processing Date" in the pamphlet Eudragit ® L, Technical application Pamphlet (info LD-12/e) from Röhm Pharma GmbH, Weiterstadt, Germany. Almost all coatings are applied in a fluid bed of he type Glatt WSG 5.

6 kg of ALCALASE ® T 2.0 is transferred to the fluid bed, and an antioxidant suspension/solution with the composition given below is applied with simultaneous drying:

480 g of sodium bisulfite
480 g of talc
120 g of $TiO_2$
240 g of carbohydrate binder
1500 g of water The above components form a coherent layer on the surface of the granules of ALCALASE ® T 2.0.

After a short intermediate drying the next (enteric) coating is applied. 2.0 kg of a 30% aqueous emulsion of Eudragit ® L 30 D is sprayed onto the particles. During the process minor samples corresponding to 1.25, 2.5, and 5% by weight of Eudragit ® L 30 D are taken out for later stability testing purposes. The process is interrupted when the coating with Eudragit ® L 30 D amounts to 10%.

Then the (acid) top coating is applied by means of an aqueous solution consisting of 120 g of citric acid
60 g of talc
30 g of hydroxypropyl cellulose (Klucel ® E)
600 g of water Now the storage stability of the final product and of the intermediate products are tested in the presence of an acid bleaching agent.

The testing conditions were as follows: 1% granulate and 99% acid bleaching composition. 30° C., 60/80% relative humidity (alternating as 60% r.h. for 8 hours, and 80% r.h. for 16 hours, etc.), open vessels.

TABLE 2

| | Coating | | | Residual activity after 3 weeks, % | |
|---|---|---|---|---|---|
| | anti-oxidant | enteric | acid | value | Standard deviation (6 single measurements) |
| Reference (ALCALASE ® T 2.0) | | | | 18.3 | 1.7 |
| Products according to the invention | 8% bisulfite | | | 22.7 | 1.2 |
| | 8% bisulfite | 1,25% Eudragit ® | | 25.8 | 2.0 |
| | 8% bisulfite | 2,5% Eudragit ® | | 29.0 | 1.5 |
| | 8% bisulfite | 5% Eudragit ® | | 32.2 | 4.1 |
| | 8% bisulfite | 10% Eudragit ® | | 35.7 | 1.1 |
| | 8% bisulfite | 10% Eudragit ® | 2% citric acid | 39.0 | 1.7 |

It clearly appears from the above table that all coatings prepared according to the invention do exhibit a significant stabilizing effect.

EXAMPLE 3

The reference composition in ALCALASE ® T 2.0 as in Example 2.

As in Example 2 the reference is coated with an antioxidant coating and with an enteric coating. Also, a reference composition similar to ALCALASE ® T 2.0 based on NaCl instead of $Na_2SO_4$ was prepared and designated ALCALASE ® T 2.0 NaCl. ALCALASE ® T 2.0 NaCl was coated with an antioxidant, and also with an antioxidant and an enteric coating, and furthermore with an antioxidant, an enteric coating, and an acid coating. All enteric coatings were performed with Eudragit ® L 30 D.

The storage stability was measured in the same manner as indicated in Example 2. The results appear from the following table.

TABLE 3

| | | Coating | | | Residual activity after n weeks, %; n = | | | |
|---|---|---|---|---|---|---|---|---|
| | | anti-oxidant | enteric | acid | 0.3 | 1 | 2 | 3 |
| | Reference (ALCALASE ® T 2.0) | | | | | 17 | 5 | <4 |
| $Na_2SO_4$ formulation | | 4% bisulfite | 10% Eudragit ® | | | 85 | 44 | 24 |
| | | 2% bisulfite | 10% Eudragit ® | | | 37 | 22 | 12 |
| | | 2% Na-ascorbate | 10% Eudragit ® | | | 45 | 27 | 20 |
| | | 1% Na- | 10% | | | 41 | 25 | 15 |

TABLE 3-continued

| | | Coating anti-oxidant | enteric | acid | Residual activity after n weeks, %; n = 0.3 | 1 | 2 | 3 |
|---|---|---|---|---|---|---|---|---|
| | | ascorbate 2% butyl hydroxy-toluene | Eudragit ® 10% Eudragit ® | | | 38 | 20 | 11 |
| | Reference (ALCALASE ® T 2.0 NaCl) | | | | <4 | | | |
| NaCl formu-lation | | 0.5% ascorbic acid | | | <4 | | | |
| | | 0.5% ascorbic acid | 10% Eudragit ® | | 18 | | | |
| | | 0.5% ascorbic acid | 10% Eudragit ® | 0.5% ascorbic acid | 14 | | | |

The clear stability enhancing effect of both the antioxidant and the enteric appears from the above table.

EXAMPLE 4

6 kg of ALCALASE® T 2.0 is transferred to the fluid bed, and a suspension/solution with the composition given below is applied with simultaneous drying:

240 g of $TiO_2$
240 g of talc
240 g of $NaHSO_3$
160 g of carbohydrate binder
1000 g of water A similar coated product, in which $NaHSO_3$ in the coating fluid is substituted by $Na_2SO_3$, is produced.

These products are coated with 10% Eudragit ® L 30 D, as in Example 2, and were tested as described in Example 2.

The storage stability was measured in the same manner as indicated in Example 2. The results appear from the following table 4.

TABLE 4

| | Coating anti-oxidant | enteric | Residual activity after n weeks, %; n = 1 | 2 | 3 |
|---|---|---|---|---|---|
| Reference (ALCALASE ® T 2.0) | | | 20 | 5 | 3 |
| | 4% $NaHSO_3$ | | 64 | 37 | 25 |
| | 4% $NaHSO_3$ | 10% Eudragit ® | 60 | 40 | 28 |
| | 4% $Na_2SO_3$ | | 64 | 41 | 26 |
| | 4% $Na_2SO_3$ | 10% Eudragit ® | 65 | 47 | 31 |

The above table clearly demonstrates the effect on the storage stability originating from the antioxidant.

EXAMPLE 5

The reference composition in this Example is ALCALASE ® T 2.0.

This reference is coated with antioxidant and/or enteric coating, basically in the same manner as indicated in Example 2, and the thus coated products are evaluated for storage stability of the enzyme.

The antioxidant coating is carried out as follows:

8 kg of ALCALASE ® T 2.0 is coated in a Lödige mixer (type FM 50) with a mixture of 3,5 kg of talc
3,5 kg of finely milled $Na_2SO_4$
0,5 kg of $TiO_2$ which is bound to the surface of the granulate by means of a binder solution consisting of 400 g of carbohydrate binder
200 g of $NaHSO_3$
1600 g of water Powder and binder solution is applied to the granulate in such manner that primarily a fifth of the powder is bound to the surface of the granulate with a fifth of the binder solution, whereafter the next fifth of the powder and the binder solution is applied, and so on. Finally the coated granulate is transferred to a spheronizer (Marumerizer ®), in which the surface is compacted and smoothed. Finally the granulate is dried in a fluid bed.

In a similar manner a granulate is produced with sodium ascorbate as antioxidant, $NaHSO_3$ in the binder solution being exchanged with sodium ascorbate.

A portion of the two antioxidant coated granulates are coated with Eudragit ® L 30 D in a fluid bed to the extent of 5 and 10% by weight.

The storage stability was measured in the same manner as indicated in Example 2. The results appear from the following table.

TABLE 5

| | Coating anti-oxidant | enteric | Residual activity after n weeks, %; n = 1 | 2 | 3 |
|---|---|---|---|---|---|
| Reference (ALCALASE ® T 2.0) | | | 19 | 5 | 2 |
| | | 10% Eudragit ® | 45 | 29 | 21 |
| | 1.4% Na-ascorbate | | 73 | 50 | 35 |
| | 1.4% Na-ascorbate | 5% Eudragit ® | 70 | 55 | 41 |
| | 1/4% Na-ascorbate | 10% Eudragit ® | 64 | 47 | 42 |
| | 1.2% $NaHSO_3$ | | 61 | 44 | 32 |
| | 1.2% $NaHSO_3$ | 5% Eudragit ® | 60 | 44 | 28 |
| | 1.2% | 10% | 57 | 44 | 27 |

TABLE 5-continued

| Coating: anti-oxidant | Coating: enteric | Residual activity after n weeks, %; n = 1 | 2 | 3 |
|---|---|---|---|---|
| $NaHSO_3$ | Eudragit ® | | | |

EXAMPLE 6

The reference in this example is ALCALASE ® T 2.0 (sulfate based).

In a Glatt WSG flue bed coatings of Eudragit ® L 30 D corresponding to 10, 20, 30, and 40%, respectively, were applied to the ALCALASE ® T 2.0 granulate.

The storage stability was measured in the same manner as indicated in Example 2 The results appear from the following table.

TABLE 6

| | Enteric coating according to the invention | Residual activity after n weeks, %; n = 1 | 2 | 3 |
|---|---|---|---|---|
| Reference (ALCALASE ® T 2.0) | | 32 | 14 | 8 |
| | 10% Eudragit ® | 77 | 54 | 33 |
| | 20% Eudragit ® | 88 | 60 | 42 |
| | 30% Eudragit ® | 81 | 58 | 40 |
| | 40% Eudragit ® | 75 | 60 | 48 |

EXAMPLE 7

6 kg of ALCALASE ® T 2.0 is transferred to a fluid bed, and a suspension/solution with the following composition is applied with simultaneous drying:

30 g of antioxidant
120 g of $TiO_2$
480 g of talc
240 g of carbohydrate binder
1500 g of water The antioxidant is either $NaHSO_3$ or $Na_2SO_3$ or a mixture thereof (126 g $Na_2SO_3$/104 g $NaHSO_3$)

The so obtained products are coated with 2.5 and 5.0% of Eudragit ® L 30 D, respectively, as described in Example 2.

The shelf stability of the products is compared to the shelf stability of ALCALASE ® T 2.0 without a protective coating and of ALCALASE ® T 2.0 coated solely with 2.5 and 5.0% of Eudragit ® L 30 D, respectively, i.e. without any antioxidant.

The testing conditions were as follows: 1% granulate and 99% acid bleaching composition, 30° C., 60/80% relative humidity, open vessels, i.e. as in Example 2.

TABLE 7

| | Coating: anti-oxidant | Coating: enteric | Residual activity after n weeks, %; n = 1 | 2 | 3 |
|---|---|---|---|---|---|
| Reference (ALCALASE ® T 2.0) | | | 48 | 18 | 15 |
| | | 2.5% Eudragit ® | 60 | 31 | 26 |
| | | 5% Eudragit ® | 61 | 40 | 31 |
| | $Na_2SO_3$ | | 63 | 38 | 27 |
| | $Na_2SO_3$ | 2.5% Eudragit ® | 74 | 43 | 39 |
| | $Na_2SO_3$ | 5% Eudragit ® | 69 | 45 | 37 |
| | $NaHSO_3$ | | 67 | 40 | 29 |
| | $NaHSO_3$ | 2.5% Eudragit ® | 73 | 46 | 37 |
| | $NaHSO_3$ | 5% Eudragit ® | 74 | 45 | 38 |
| | $Na_2SO_3$/ $NaHSO_3$ | | 71 | 39 | 29 |
| | $Na_2SO_3$/ $NaHSO_3$ | 2.5% Eudragit ® | 76 | 46 | 36 |
| | $Na_2SO_3$/ $NaHSO_3$ | 5% Eudragit ® | 74 | 47 | 37 |

I claim:

1. An additive for detergency purposes comprising an acidic bleaching agent and a granulate detergent enzyme product, said enzyme product further comprising a core of a microbial enzyme-containing material, a coating thereon, and an overcoating on the coating wherein the coating comprises an enteric coating agent, which is a copolymer of (meth) acrylic acid and a (meth) acrylic acid derivative, more than 90% of the enzyme granulate cores exhibiting particle sizes between 2 and 2000 μm wherein the weight of coating agent applied to the granulate core is between 5 and 30% of the weight of the enzyme product, wherein said enzyme product contains an anti-oxidant as part of the enteric agent coating or in a separate undercoating, and wherein the particles further comprise an acid material containing coating as said overcoating on the coating.

2. A product according to claim 1, wherein the copolymer is a copolymer of (meth)acrylic acid and a (meth)acrylic acid ester.

3. A product according to claim 2, wherein the copolymer is a copolymer of methacrylic acid and methacrylic acid methyl ester.

4. A product according to claim 1 wherein the coating agent contains between 25 and 100% of the enteric coating agent on a dry substance basis.

5. A product according to claim 1, wherein the coating also comprises one or both of a filler and plasticizer.

6. A product according to claim 1, wherein the enzyme is selected from the group consisting of protease, amylase, lipase, cellulase, and oxidase.

7. A product according to claim 1 wherein the particles further comprise an antioxidant containing coating as an undercoat to the enteric coating.

8. A product according to claim 1 wherein more than 90% of the enzyme granulate cores exhibit particle sizes between 250 and 2000 μm.

9. A product according to claim 1 wherein more than 90% of the enzyme granulate cores exhibit particles sizes between 250 and 1000 μm.

10. A product according to claim 1 wherein more than 90% of the enzyme granulate cores exhibit a particle sizes between 2 and 100 μm and said product is in slurry form.

11. A product according to claim 1, and further comprising a coating that contains one or both of an antioxidant and acid material.

* * * * *